United States Patent
Lee et al.

(10) Patent No.: US 8,965,490 B2
(45) Date of Patent: Feb. 24, 2015

(54) SYSTEMS AND METHODS FOR DETECTION OF THE SUPERIOR VENA CAVA AREA

(71) Applicants: Kichang Lee, Newton, MA (US); Brian J. Wenzel, San Jose, CA (US); Jin Jiang, San Carlos, CA (US); Stephen P. Hanlon, San Ramon, CA (US)

(72) Inventors: Kichang Lee, Newton, MA (US); Brian J. Wenzel, San Jose, CA (US); Jin Jiang, San Carlos, CA (US); Stephen P. Hanlon, San Ramon, CA (US)

(73) Assignee: Vasonova, Inc., Menol Park, CA (US)

( * ) Notice: Subject to any disclaimer, the term of this patent is extended or adjusted under 35 U.S.C. 154(b) by 0 days.

(21) Appl. No.: 13/829,650

(22) Filed: Mar. 14, 2013

(65) Prior Publication Data

US 2013/0296725 A1 Nov. 7, 2013

Related U.S. Application Data

(60) Provisional application No. 61/643,890, filed on May 7, 2012, provisional application No. 61/643,888, filed on May 7, 2012, provisional application No. 61/649,196, filed on May 18, 2012, provisional application No. 61/649,172, filed on May 18, 2012.

(51) Int. Cl.
| | |
|---|---|
| *A61B 5/0452* | (2006.01) |
| *A61B 8/08* | (2006.01) |
| *A61B 5/06* | (2006.01) |

(Continued)

(52) U.S. Cl.
CPC .............. *A61B 8/0841* (2013.01); *A61B 5/061* (2013.01); *A61B 8/488* (2013.01); *A61B 5/04012* (2013.01); *A61B 5/0456* (2013.01); *A61B 8/12* (2013.01)
USPC ........................................................ 600/509

(58) Field of Classification Search
CPC ................................ A61B 5/06; A61B 5/0452
See application file for complete search history.

(56) References Cited

U.S. PATENT DOCUMENTS

| | | |
|---|---|---|
| 3,565,062 A | 2/1971 | Kuris |
| 4,143,650 A | 3/1979 | Hatke |

(Continued)

FOREIGN PATENT DOCUMENTS

| | | |
|---|---|---|
| EP | 0917069 A1 | 5/1999 |
| EP | 1181895 A2 | 2/2002 |

(Continued)

OTHER PUBLICATIONS

Benchimol et al.; Right atrium and superior vena cava flow velocity in man measured with the doppler-catheter flowmeter-telemetry system; The Amer. J of Med.; vol. 48; pp. 303-309; Mar. 1970.

(Continued)

*Primary Examiner* — Michael Kahelin

(74) *Attorney, Agent, or Firm* — Baker & Hostetler LLP

(57) ABSTRACT

Described herein are systems, devices and methods to increase the accuracy of intravascular catheter placement, and to improve electrocardiogram (ECG), intravascular electrogram, and ultrasound Doppler signal processing to detect the Superior Vena Cava (SVC) area. Embodiments of the invention are intended to place an intravascular catheter within the lower ⅓ of SVC to the junction of the SVC and the right atrium (RA)—called the cavoatrial junction (CAJ). In particular, the improved accuracy of CAJ location detection during an intravascular catheter placement can be provided by optimization of ECG parameters and ultrasound Doppler signal using Neuro-Fuzzy logic and/or other processing techniques.

15 Claims, 14 Drawing Sheets

(51) Int. Cl.
*A61B 5/04* (2006.01)
*A61B 5/0456* (2006.01)
*A61B 8/12* (2006.01)

(56) References Cited

U.S. PATENT DOCUMENTS

| | | | |
|---|---|---|---|
| 4,324,258 A | 4/1982 | Huebscher et al. |
| 4,354,502 A | 10/1982 | Colley et al. |
| 4,503,861 A | 3/1985 | Entrekin |
| 4,549,879 A | 10/1985 | Groshong et al. |
| 4,644,960 A | 2/1987 | Johans |
| 4,667,679 A | 5/1987 | Sahota |
| 4,692,148 A | 9/1987 | Kantrowitz et al. |
| 4,706,681 A | 11/1987 | Breyer et al. |
| 4,790,831 A | 12/1988 | Skribiski |
| 4,849,172 A | 7/1989 | Yafuso et al. |
| 4,856,529 A | 8/1989 | Segal |
| 4,896,677 A | 1/1990 | Kaneko et al. |
| 4,966,148 A | 10/1990 | Millar |
| 4,967,753 A | 11/1990 | Haase et al. |
| 4,979,510 A | 12/1990 | Franz et al. |
| 5,038,789 A | 8/1991 | Frazin et al. |
| 5,046,497 A | 9/1991 | Millar |
| 5,047,930 A | 9/1991 | Martens et al. |
| 5,058,597 A | 10/1991 | Onoda et al. |
| 5,078,148 A | 1/1992 | Nassi et al. |
| 5,078,678 A | 1/1992 | Katims |
| 5,107,841 A | 4/1992 | Sturgill |
| 5,174,295 A | 12/1992 | Christian et al. |
| 5,190,045 A | 3/1993 | Frazin |
| 5,207,226 A | 5/1993 | Bailin et al. |
| 5,220,924 A | 6/1993 | Frazin |
| 5,269,289 A | 12/1993 | Takehana et al. |
| 5,271,404 A | 12/1993 | Corl et al. |
| 5,311,871 A | 5/1994 | Yock |
| 5,431,628 A | 7/1995 | Millar |
| 5,477,858 A | 12/1995 | Norris et al. |
| 5,492,125 A | 2/1996 | Kim et al. |
| 5,546,949 A | 8/1996 | Frazin et al. |
| 5,566,674 A | 10/1996 | Weng |
| 5,575,286 A | 11/1996 | Weng et al. |
| 5,588,432 A | 12/1996 | Crowley |
| 5,640,961 A | 6/1997 | Verdonk |
| 5,657,760 A | 8/1997 | Ying et al. |
| 5,666,958 A | 9/1997 | Rothenberg et al. |
| 5,669,389 A | 9/1997 | Rotteveel et al. |
| 5,693,032 A | 12/1997 | Bierman |
| 5,697,377 A | 12/1997 | Wittkampf et al. |
| 5,722,959 A | 3/1998 | Bierman |
| 5,733,323 A | 3/1998 | Buck et al. |
| 5,749,364 A | 5/1998 | Sliwa et al. |
| 5,782,766 A | 7/1998 | Weng et al. |
| 5,785,657 A | 7/1998 | Breyer et al. |
| 5,795,298 A | 8/1998 | Vesely et al. |
| 5,803,083 A | 9/1998 | Buck et al. |
| 5,857,973 A | 1/1999 | Ma et al. |
| 5,860,951 A | 1/1999 | Eggers et al. |
| 5,876,342 A | 3/1999 | Chen et al. |
| 5,878,746 A | 3/1999 | Lemelson et al. |
| 5,891,036 A | 4/1999 | Izumi |
| 5,897,488 A | 4/1999 | Ueda |
| 5,908,385 A | 6/1999 | Chechelski et al. |
| 5,935,143 A | 8/1999 | Hood |
| 5,938,603 A | 8/1999 | Ponzi |
| 5,999,846 A | 12/1999 | Pardey et al. |
| 6,007,491 A | 12/1999 | Ling et al. |
| 6,059,731 A | 5/2000 | Seward et al. |
| 6,083,170 A | 7/2000 | Ben-Haim |
| 6,120,445 A | 9/2000 | Grunwald |
| 6,179,781 B1 | 1/2001 | Phillips |
| 6,179,782 B1 | 1/2001 | Cuce |
| 6,213,947 B1 | 4/2001 | Phillips |
| 6,251,073 B1 | 6/2001 | Imran et al. |
| 6,264,611 B1 | 7/2001 | Ishikawa et al. |
| 6,364,838 B1 | 4/2002 | Freiburger et al. |
| 6,500,130 B2 | 12/2002 | Kinsella et al. |
| 6,520,916 B1 | 2/2003 | Brennen |
| 6,542,626 B1 | 4/2003 | Brouwer et al. |
| 6,551,244 B1 | 4/2003 | Gee |
| 6,556,695 B1 | 4/2003 | Packer et al. |
| 6,561,979 B1 | 5/2003 | Wood et al. |
| 6,591,144 B2 | 7/2003 | Pigott |
| 6,594,524 B2 | 7/2003 | Esteller et al. |
| 6,612,992 B1 | 9/2003 | Hossack et al. |
| 6,638,243 B2 | 10/2003 | Kupiecki |
| 6,685,648 B2 | 2/2004 | Flaherty et al. |
| 6,689,119 B1 | 2/2004 | Di Caprio et al. |
| 6,695,785 B2 | 2/2004 | Brisken et al. |
| 6,704,590 B2 | 3/2004 | Haldeman |
| 6,719,756 B1 | 4/2004 | Muntermann |
| 6,733,454 B1 | 5/2004 | Bakircioglu et al. |
| 6,740,590 B1 | 5/2004 | Yano et al. |
| 6,749,606 B2 | 6/2004 | Keast et al. |
| 6,814,702 B2 | 11/2004 | Redano |
| 6,866,677 B2 | 3/2005 | Douk et al. |
| 6,896,658 B2 | 5/2005 | Ji et al. |
| 6,931,269 B2 | 8/2005 | Terry |
| 6,973,352 B1 | 12/2005 | Tsutsui et al. |
| 7,037,290 B2 | 5/2006 | Gardeski et al. |
| 7,043,293 B1 | 5/2006 | Baura |
| 7,150,716 B2 | 12/2006 | Jones et al. |
| 7,200,435 B2 | 4/2007 | Ricci et al. |
| 7,204,798 B2 | 4/2007 | Zdeblick et al. |
| 7,225,013 B2 | 5/2007 | Geva et al. |
| 7,346,393 B2 | 3/2008 | Spinelli et al. |
| 7,367,949 B2 | 5/2008 | Korhonen et al. |
| 7,393,501 B2 | 7/2008 | Zumeris et al. |
| 7,422,563 B2 | 9/2008 | Roschak et al. |
| 7,433,853 B2 | 10/2008 | Brockway et al. |
| 7,485,095 B2 | 2/2009 | Shusterman |
| 7,599,730 B2 | 10/2009 | Hunter et al. |
| 7,627,386 B2 | 12/2009 | Mo et al. |
| 7,640,055 B2 | 12/2009 | Geva et al. |
| 7,668,579 B2 | 2/2010 | Lynn |
| 7,697,972 B2 | 4/2010 | Verard et al. |
| 7,708,696 B2 | 5/2010 | Ritter et al. |
| 7,733,224 B2 | 6/2010 | Tran |
| 7,794,407 B2 | 9/2010 | Rothenberg |
| 7,833,221 B2 | 11/2010 | Voegele et al. |
| 7,966,061 B2 | 6/2011 | Al-Abed et al. |
| 7,981,038 B2 | 7/2011 | Kanade et al. |
| 7,991,458 B2 | 8/2011 | Hardahl et al. |
| 8,046,052 B2 | 10/2011 | Verard et al. |
| 8,052,648 B2 | 11/2011 | Dikeman et al. |
| 8,060,185 B2 | 11/2011 | Hunter et al. |
| 8,409,103 B2 | 4/2013 | Grunwald et al. |
| 2002/0045810 A1 | 4/2002 | Ben-Haim |
| 2002/0087156 A1 | 7/2002 | Maguire et al. |
| 2002/0111548 A1 | 8/2002 | Swanson et al. |
| 2002/0151790 A1 | 10/2002 | Abend |
| 2002/0156363 A1 | 10/2002 | Hunter et al. |
| 2002/0168618 A1 | 11/2002 | Anderson et al. |
| 2002/0188257 A1 | 12/2002 | Bierman |
| 2003/0083717 A1 | 5/2003 | Mlynski et al. |
| 2003/0109785 A1 | 6/2003 | Buck et al. |
| 2004/0011358 A1 | 1/2004 | Smaldone et al. |
| 2004/0039436 A1 | 2/2004 | Spenser et al. |
| 2004/0102719 A1 | 5/2004 | Keith et al. |
| 2004/0116809 A1 | 6/2004 | Chow et al. |
| 2004/0116969 A1 | 6/2004 | Owen et al. |
| 2004/0158143 A1 | 8/2004 | Flaherty et al. |
| 2004/0254523 A1 | 12/2004 | Fitzgerald et al. |
| 2005/0085718 A1 | 4/2005 | Shahidi |
| 2005/0148836 A1 | 7/2005 | Kleen et al. |
| 2005/0159738 A1 | 7/2005 | Visram et al. |
| 2006/0079868 A1 | 4/2006 | Makin et al. |
| 2006/0084883 A1 | 4/2006 | Linker |
| 2006/0094923 A1 | 5/2006 | Mate |
| 2007/0016069 A1 | 1/2007 | Grunwald et al. |
| 2007/0016070 A1 | 1/2007 | Grunwald et al. |
| 2007/0016072 A1 | 1/2007 | Grunwald et al. |
| 2007/0167738 A1 | 7/2007 | Timinger et al. |
| 2007/0265526 A1 | 11/2007 | Govari et al. |
| 2007/0276334 A1 | 11/2007 | Bierman et al. |

(56) References Cited

U.S. PATENT DOCUMENTS

| | | | |
|---|---|---|---|
| 2007/0299352 A1* | 12/2007 | Harlev et al. ............... 600/509 |
| 2008/0058607 A1 | 3/2008 | Watrous |
| 2008/0161669 A1 | 7/2008 | Hauck et al. |
| 2008/0188740 A1 | 8/2008 | Diaz et al. |
| 2009/0005675 A1 | 1/2009 | Grunwald et al. |
| 2009/0118612 A1 | 5/2009 | Grunwald et al. |
| 2009/0143740 A1 | 6/2009 | Bierman et al. |
| 2009/0156926 A1 | 6/2009 | Messerly et al. |
| 2009/0177090 A1 | 7/2009 | Grunwald et al. |
| 2009/0182283 A1 | 7/2009 | Sloan |
| 2009/0234328 A1 | 9/2009 | Cox et al. |
| 2009/0259124 A1 | 10/2009 | Rothenberg |
| 2009/0262977 A1 | 10/2009 | Huang et al. |
| 2009/0287070 A1 | 11/2009 | Baker, Jr. |
| 2009/0287191 A1 | 11/2009 | Ferren et al. |
| 2010/0036227 A1 | 2/2010 | Cox et al. |
| 2010/0204569 A1 | 8/2010 | Burnside et al. |
| 2011/0087114 A1 | 4/2011 | Moulder |
| 2011/0196248 A1 | 8/2011 | Grunwald |
| 2011/0257600 A1 | 10/2011 | Kessler |
| 2011/0282187 A1 | 11/2011 | Harlev et al. |
| 2011/0317006 A1 | 12/2011 | Kuboyama et al. |
| 2012/0035434 A1 | 2/2012 | Ferren et al. |
| 2012/0083702 A1 | 4/2012 | Ingold, Jr. et al. |
| 2012/0136242 A1 | 5/2012 | Qi et al. |

FOREIGN PATENT DOCUMENTS

| | | |
|---|---|---|
| JP | 62500703 A | 3/1987 |
| JP | 62-236532 | 10/1987 |
| JP | H3205040 A | 9/1991 |
| JP | H4017843 | 1/1992 |
| JP | U-7-3608 | 1/1995 |
| JP | H07505791 A1 | 6/1995 |
| JP | 08-229044 | 9/1995 |
| JP | 09-253084 | 9/1997 |
| JP | 10-277039 | 10/1998 |
| JP | 2004500210 | 1/2004 |
| JP | 2004130114 | 4/2004 |
| JP | 2006513731 | 4/2006 |
| KR | 1020090019762 | 2/2009 |
| WO | WO98/08440 A1 | 3/1998 |
| WO | WO01/70303 A2 | 9/2001 |
| WO | WO2006/051523 A2 | 5/2006 |
| WO | WO2007/047360 A2 | 4/2007 |

OTHER PUBLICATIONS

Benchimol et al.; Bidirectional blood flow velocity in the cardiac chambers and great vessels studied with the doppler ultrasonic flowmeter; The Amer. J of Med.; vol. 52; pp. 467-473; Apr. 1972.

Bowers et al.; Respiratory rate derived from principal component analysis of single lead electrocardiogram; Conference Proc.; Computers in Cardiology; Bologna, IT; 2008; vol. 35; pp. 437-440; Sep. 14-17, 2008.

Bidoggia et al.; Transseptal left heart catheterization: usefulness of the intracavitary electrocardiogram in the localization of the fossa ovalis; Catheterization and Cardiovascular Diagnosis; New York, NY; vol. 24; No. 3; pp. 221-225; Nov. 1, 1991.

Bossert et al.; Swan-Ganz catheter-induced severe complications in cardiac surgery: right ventricular perforation, knotting, and rupture of a pulmonary artery; J. Car. Surg.; vol. 21; No. 3; pp. 292-295; May/Jun. 2006.

Brunner, Eberhard; Ultrasound system considerations and their impact on front-end components; Analog Devices, Inc.; pp. 1-19; May-Jun. 2002.

Fearon et al.; Evaluating intermediate coronary lesions in the cardiac catheterization laboratory; Rev Cardiovasc Med; vol. 4; No. 1; pp. 1-7; Winter 2003.

Hellerstein et al.; Recording of intracavity potentials through a single lumen, saline filled cardiac catheter; P.S.E.B.M.,; vol. 71; pp. 58-60; Apr. 5, 1949.

Kalmanson et al.; Letter to the Editor; "Directional vs bidirectional doppler velocimeter"; Am. Heart J.; vol. 83; No. 3; pp. 437; Mar. 1972.

Lewis et al.; A Study of Normal and abnormal femoral venous flow velocity using a directional doppler; Br. J. Surg: vol. 59, No. 4; pp. 303; Apr. 1972.

McGee, et al.; Accurate placement of central venous catheters: A prospecitve, randomized, multicenter trial; Critical Care Medicine, vol. 21, No. 8, pp. 1118-1123, Aug. 1993.

Naylor; Reduction of malposition in peripherally inserted central catheters with tip location system; JAVA; vol. 12; No. 1; pp. 29-31; Spring 2007.

Pittiruti et al.; The EKG method for positioning the tip of PICCs; results from two preliminary studies;JAVA; vol. 13; No. 4; pp. 112-119; Winter 2008.

Radke et al.; Control of the placement of a central venous catheter using doppler ultrasound; Der Anaesthesist 1990-05; vol. 39; No. 5; pp. 283-287; May 1990.

Starr, et al.; EKG guided placement of subclavian CVP catheters using J-wire; Ann. Surg.; vol. 204, No. 6, pp. 673-676, Dec. 1986.

Stas et al.; Peroperative intravasal electrographic control of catheter tip position in access ports placed by venous cut-down technique;EJSO; vol. 27; pp. 316-320; Apr. 2001.

Schummer et al.; Central venous catheters—the inability of 'intra-atrial ECG' to prove adequate positioning; British Jour. Of Anaesthesia, vol. 93, No. 2; pp. 193-198, Jun. 25, 2004.

Grunwald et al.; U.S. Appl. No. 13/844,408 entitled "Apparatus and method for endovascular device guiding and positioning using physiological parameters," filed Mar. 15, 2013.

Wenzel et al.; U.S. Appl. No. 13/829,522 entitled "Right atrium indicator," filed Mar. 14, 2013.

* cited by examiner

FIGURE 2. A stylet with an intravascular ECG electrode.

FIGURE 3. A typical ECG wave and its components.

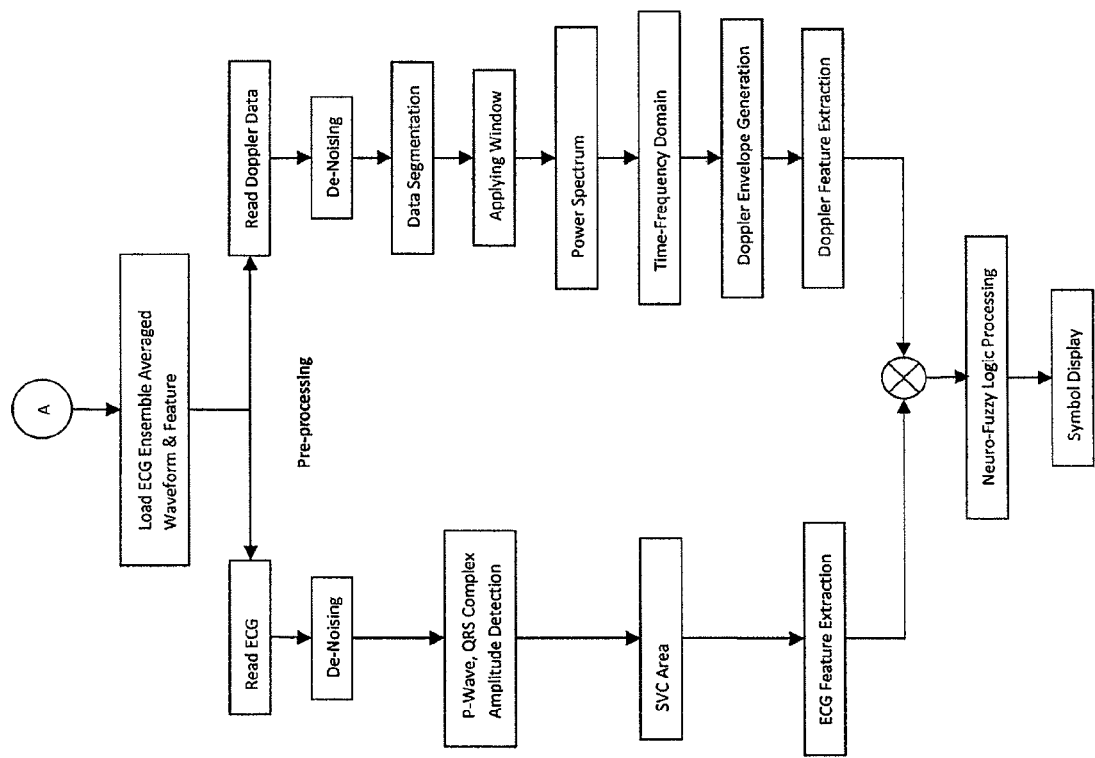
Figure 10 Flow charts of the pre-processing and processing of the ECG and Doppler data to obtain the output results.

SYSTEMS AND METHODS FOR DETECTION OF THE SUPERIOR VENA CAVA AREA

CROSS REFERENCE TO RELATED APPLICATIONS

This application claims priority to U.S. Provisional Application No. 61/643,890 filed May 7, 2012, titled "SYSTEMS AND METHODS FOR DETECTION OF THE SUPERIOR VENA CAVA AREA AND THE CAVOATRIAL JUNCTION," U.S. Provisional Application No. 61/643,888 filed May 7, 2012, titled "RIGHT ATRIUM INDICATOR," U.S. Provisional Application No. 61/649,196 filed May 18, 2012, titled "SYSTEMS AND METHODS FOR DETECTION OF THE SUPERIOR VENA CAVA AREA AND THE CAVOATRIAL JUNCTION," and U.S. Provisional Application No. 61/649,172 filed May 18, 2012, titled "RIGHT ATRIUM INDICATOR," each of which is hereby incorporated by reference in its entirety for all purposes.

INCORPORATION BY REFERENCE

All publications and patent applications mentioned in this specification are herein incorporated by reference to the same extent as if each individual publication or patent application was specifically and individually indicated to be incorporated by reference.

FIELD

Embodiments of the invention relate, in general, to an endovascular navigation system and methods for guiding and positioning an endovascular device using an algorithm-based artificial intelligence processor.

BACKGROUND

Intravascular catheters, including peripherally inserted central catheters (PICC) and central venous catheters (CVC), have been used to provide therapy, administer pharmacological and/or nutritional agents, and meet other clinical needs such as hemodialysis, blood drawing, and so on. In general, it is recommended that the appropriate location of an intravascular catheter is the lower ⅓ of the superior vena cava (SVC) to the junction of the SVC and right atrium (RA), also known as the cavoatrial junction (CAJ) region, as shown in FIG. 1. However, due to a variety of factors, such as tortuous venous pathway, venous anomaly, and incorrect initial estimation, approximately 5-32% of all PICC line placements result in malposition. This malposition can result in both clinically and financially adverse outcomes, such as increased infection risk, thrombosis, cardiac tamponade and/or additional chests X-ray exposure. To prevent or reduce possible adverse outcomes, a PICC line should generally be located at the desired location in the lower ⅓ of the SVC to CAJ.

ECG-guided intravascular catheterization, such as PICC catheterization, has been used to reduce the chance of PICC/CAC line malposition by means of an electrocardiogram (ECG) sensor equipped stylet, which is a wire-like slender medical device, as illustrated in FIG. 2. ECGs have long been used for evaluating heart condition by recording and monitoring the electrical activities of the heart. The ECG can be used for various clinical applications. One example is the detection of abnormal electrical patterns and/or morphology of ill patients, aiding in the diagnosis of cardiovascular disease, and guiding therapeutic decisions. Another example is assisting clinicians to advance a PICC or CVC to the CAJ area.

During each heart beat cycle, the heart cells change the membrane potential, and repeat the "depolarization—reduction (less negative) of the electrical charge (membrane potential) toward zero" and "repolarization—returning of the membrane potential to a negative resting potential" process. During each cardiac cycle, a heart orderly progresses (or spreads) an electrical charge from the atrium, triggered by the pacemaker cells in the sinoatrial (SA) node, throughout the heart muscle through the conduction pathways in the heart. This progression of electrical wave is detected as tiny rises and falls in the voltage among electrodes placed around the heart.

A typical ECG wave of the cardiac cycle includes a P wave, a QRS complex, a T wave, and a U wave which is not always visible, as shown in FIG. 3. During atrial depolarization, an electrical charge spreads from the SA node to the right atrium, then the left atrium. This turns into the P wave. The QRS complex represents the rapid depolarization of the right and left ventricles. The T wave indicates the repolarization of the right and left ventricles.

The current prevailing ECG-guided catheterization method is to estimate the catheter tip location by monitoring the P wave amplitude change. However, this method has several limitations to accuracy and practicality when navigating through the venous system. One example is the abnormality of the P wave with arrhythmia or abnormal heart activity, which can render standard techniques inoperable. Due to these limitations, a conventional ECG-guided catheterization generally requires confirmation of the final catheter tip location with fluoroscopy and/or a post-operative chest X-ray which results in additional cost and X-ray exposure.

Accordingly, it would be desirable to provide an endovenous access and guidance system that overcomes the shortcomings of the prior art devices described above.

SUMMARY OF THE DISCLOSURE

The present invention relates an endovascular navigation system and methods for guiding and positioning an endovascular device using an algorithm-based artificial intelligence processor.

In some embodiments, a method for determining the location of a medical device within a body is provided. The method includes inserting the medical device into the venous vasculature of the body; measuring an initial ECG waveform using an intravascular ECG electrode after the insertion; advancing the medical device within the venous vasculature of the body; measuring a second ECG waveform using the intravascular ECG electrode after the medical device has been advanced; extracting one or more feature values from the initial ECG waveform and the second ECG waveform, the one or more feature values including one or more initial feature values from the initial ECG waveform and one or more beat-to-beat feature values from the second ECG waveform; determining one or more ratios between the one or more initial feature values and the corresponding one or more beat-to-beat feature values; comparing the one or more ratios with corresponding one or more threshold feature values; and determining whether the device is at a target location based on the comparison of the one or more ratios with the one or more threshold feature values.

In some embodiments, the target location is the SVC.

In some embodiments, the one or more feature values includes a QRS complex amplitude.

In some embodiments, the one or more feature values includes a T wave amplitude.

In some embodiments, the one or more feature values includes an amplitude difference between R and S waves.

In some embodiments, the one or more feature values includes an area under a QRS complex.

In some embodiments, the one or more feature values includes an area under a T waveform.

In some embodiments, the method further includes measuring an external ECG waveform and determining a QRS complex amplitude of the external ECG waveform.

In some embodiments, the method further includes determining a ratio of the QRS complex amplitude of the internal ECG waveform to the QRS complex amplitude of the external ECG waveform.

In some embodiments, the method further includes determining that the medical device is in the SVC when the QRS complex amplitude of the internal ECG waveform is greater than a first threshold and the ratio of the QRS complex amplitude of the internal ECG waveform to the QRS complex amplitude of the external ECG waveform is greater than or equal to a QRS complex amplitude ratio threshold. In some embodiments, the first QRS complex amplitude ratio threshold is 1.4.

In some embodiments, the method further includes determining that the medical device is in the SVC when the QRS complex amplitude of the internal ECG waveform is greater than or equal to half of a first threshold but less than the first threshold, and the ratio of the QRS complex amplitude of the internal ECG waveform to the QRS complex amplitude of the external ECG waveform is greater than or equal to a QRS complex amplitude ratio threshold. In some embodiments, the first QRS complex amplitude ratio threshold is 1.6.

In some embodiments, the method further includes determining that the medical device is in the SVC when the QRS complex amplitude of the internal ECG waveform is less than half of a first threshold, and the ratio of the QRS complex amplitude of the internal ECG waveform to the QRS complex amplitude of the external ECG waveform is greater than or equal to a QRS complex amplitude ratio threshold. In some embodiments, the first QRS complex amplitude ratio threshold is 1.8.

In some embodiments, the one or more feature values are extracted from ensemble averaged ECG waveforms.

In some embodiments, a system for determining the location of a medical device within a body is provided. The system includes an elongate body having an intravascular ECG electrode disposed on a distal portion of the elongate body; a processor configured to receive and process an ECG signal from the intravascular ECG electrode; and memory for storing instructions, which when executed by the processor, causes the processor to: measure an initial ECG waveform using an intravascular ECG electrode after the insertion; measure a second ECG waveform using the intravascular ECG electrode after the medical device has been advanced; extract one or more feature values from the initial ECG waveform and the second ECG waveform, the one or more feature values including one or more initial feature values from the initial ECG waveform and one or more beat-to-beat feature values from the second ECG waveform; determine one or more ratios between the one or more initial feature values and the corresponding one or more beat-to-beat feature values; compare the one or more ratios with corresponding one or more threshold feature values; and determine whether the device is at a target location based on the comparison of the one or more ratios with the one or more threshold feature values.

In some embodiments, the target location is the SVC.

In some embodiments, the one or more feature values includes a QRS complex amplitude.

In some embodiments, the one or more feature values includes a T wave amplitude.

In some embodiments, the one or more feature values includes an amplitude difference between R and S waves.

In some embodiments, the one or more feature values includes an area under a QRS complex.

In some embodiments, the one or more feature values includes an area under a T waveform.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 10 shows a flow chart of an embodiment of the preprocessing and processing of the ECG and Doppler data;

DETAILED DESCRIPTION

Figure 1:
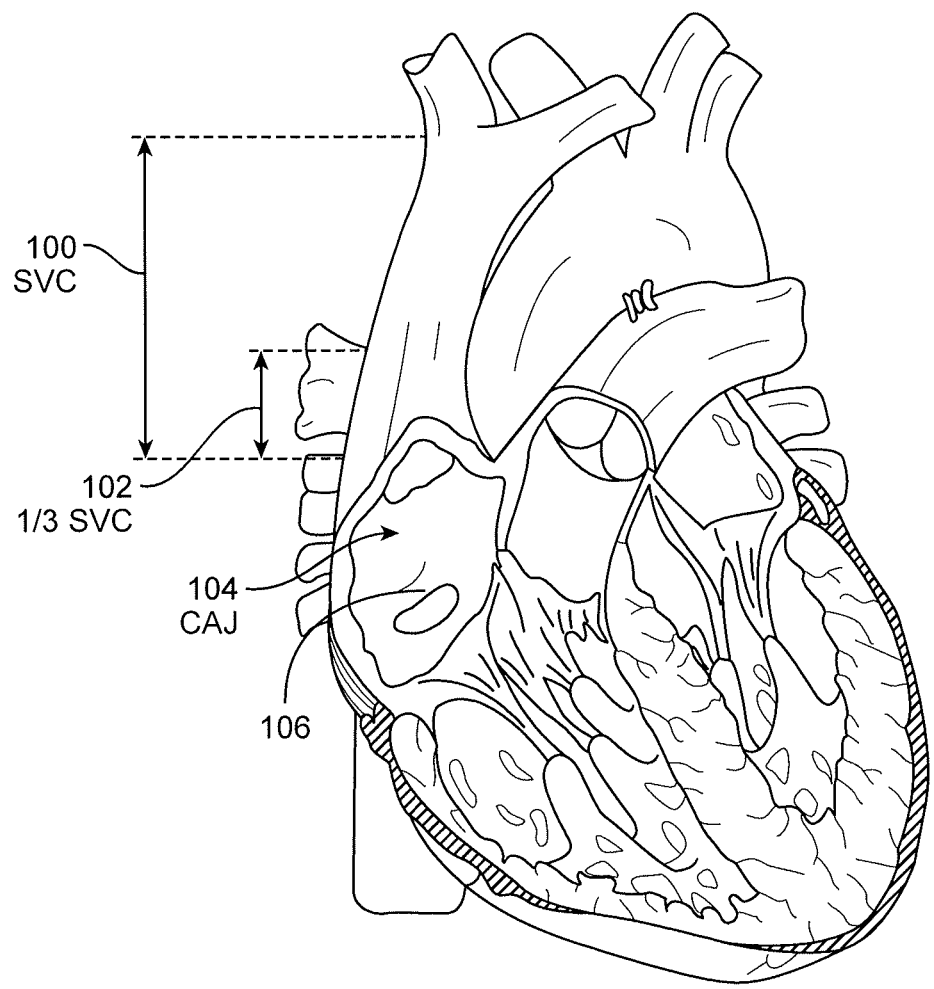
FIG. 1 is shows the anatomy of the superior vena cava (SVC) and cavoatrial junction (CAJ)
Figure 2:
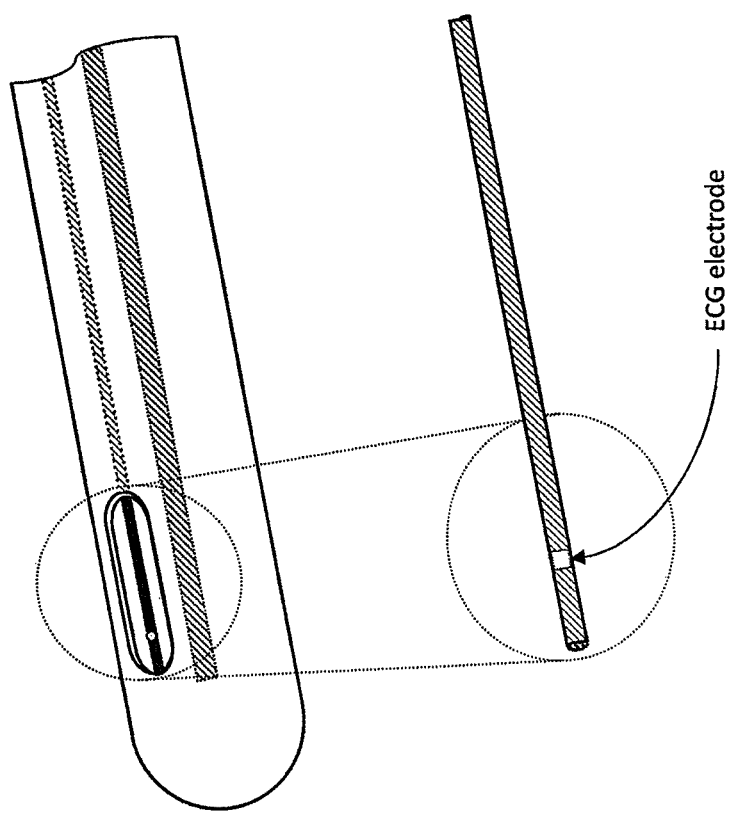
FIG. 2 shows a stylet with an intravascular ECG electrode.
Figure 3:
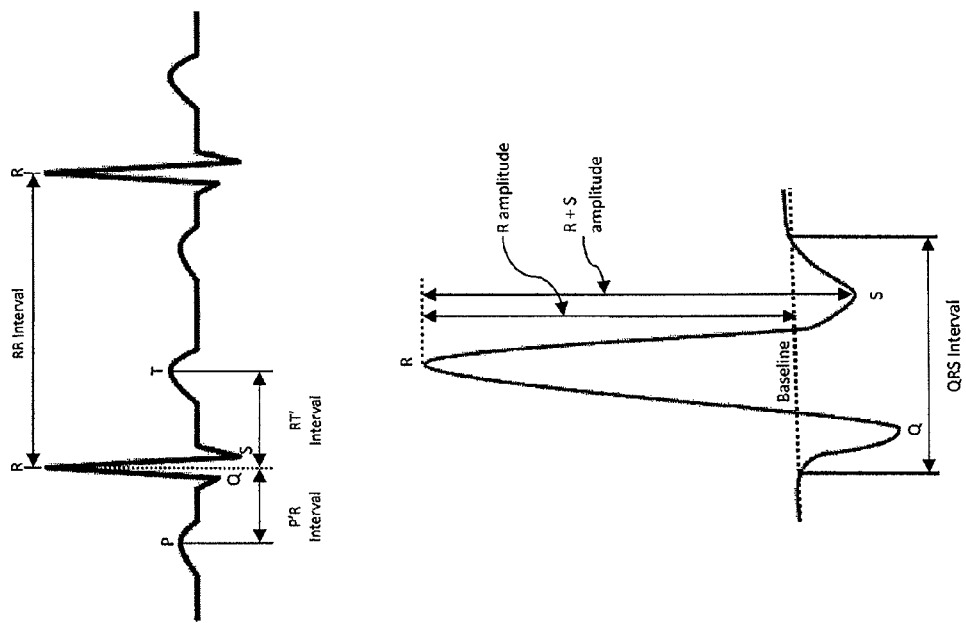
FIG. 3 shows a typical ECG wave and its components.

Described herein are systems, devices and methods to increase the accuracy of intravascular catheter placement, and to improve ECG, intravascular electrogram, and ultrasound Doppler signal processing to detect SVC area. Embodiments of the invention are intended to place an intravascular catheter within the lower ⅓ of SVC to the junction of the SVC and the RA—called the CAJ. In particular, the improved accuracy of CAJ location detection during an intravascular catheter placement can be provided by optimization of ECG parameters and ultrasound Doppler signal using Neuro-Fuzzy logic and/or other processing techniques.

In an exemplary embodiment, Doppler and/or ECG signals are used to determine the catheter tip location. In various embodiments, the system makes use of the fact that, during the catheter insertion, the physiological characteristics of the input signals are different in different positions. In various embodiments, artificial intelligence is used to derive positional information from the sensor signals to guide the tip to and land at optimal desired position (e.g. the lower ⅓ of SVC and the catheter tip heading to RA). The two signals are amplified, sampled, and filtered along with other appropriate pre-processing operations to render the signal information as one or more features. These features become inputs to a processor. The processor then processes the input and outputs a result indicative of the position and/or direction of the tip. Parameters associated with the feature and algorithms generally include constants, coefficients and weighing factors, for example, that can be adjusted to fine tune the algorithms.

In an exemplary Doppler channel, the transmitter center frequency is about 11.667 MHz, outputting a burst of about 8 pulses at a pulse repetition frequency (PRF) of approximately 30 kHz. The received Doppler signal may be amplified, sampled, down-converted or otherwise appropriately subjected to operations to yield features used as inputs to the guidance system, and in particular, the pre-processor.

The operating frequency and PRF typically depend on the hardware and the device environment. The exemplary system for insertion and navigation in the venous environment has a selected operating frequency of between about 8 MHz and about 15 MHz, and in various respects between about 10 MHz to about 12 MHz. In various embodiments, the operating frequency is about 12 MHz. The operating frequency may be higher or lower depending on the applications. For example, conventional coronary artery systems operate at around 20 MHz.

The PRF drives the signal generation and acquisition. Among other things, the PRF in combination with the operating frequency determines the resolution of the signal. For example, if the PRF is too low the system will not acquire useful data. Generally, a higher PRF provides more flow information but emits more energy into the patient. Thus, if the PRF is too high the system may present a health risk to the patient. In various embodiments, the PRF is between about 30 kHz to about 45 kHz. In various embodiments, the PRF is below 60 kHz, below 50 kHz, below 40 kHz, or below 30 kHz. In various embodiments, the PRF is about 30 kHz or about 40 kHz. By contrast, the PRF needs to be significantly higher for use in the arterial system. Typically, PRF must be around 100 kHz or higher in the arterial system.

Various aspects of the invention relate to the use of intravascularly-measured physiological parameters for locating, guiding, and placing catheters in the vasculature. Various aspects of the invention relate to an endovascular member assembly with built-in sensors for measuring of physiological parameters such as blood flow, velocity, and pressure. Various aspects of the invention relate to an assembly for further measuring intravascular ECG.

Various aspects of the invention relate to data processing algorithms that can identify and recognize different locations in the vasculature based on the pattern of physiological parameters measured at that location.

Various aspects of the present invention relate to data processing algorithms that can identify and recognize structures such as objects of interest in the vasculature, for example, blood clots based on the pattern of parameters measured (e.g., A-mode and blood flow velocity). Various aspects of the invention relate to an instrument that has a user interface which shows guiding and positioning information and presents the objects of interest (e.g. blood clots). For example, in this aspect the processor is further configured to process a signal from the non-image ultrasound transducer and to indicate in the output device information related to the presence of a structure in the field of view of the non-imaging ultrasound transducer. In various embodiments, the system can draw conclusions from the location information and even make recommendations to the user.

Various aspects of the invention relate to a method of guiding and positioning an endovascular device within the vasculature by the user based on location information provided by the sensor-based endovascular device. Other various aspects of embodiments the invention relate to the use of intravascularly measured physiological parameters for locating, guiding, and placing catheters or stylets or guide wires for use as guides to particular locations within the vasculature that have been identified using the guided vascular access devices and systems described herein.

Figure 4:
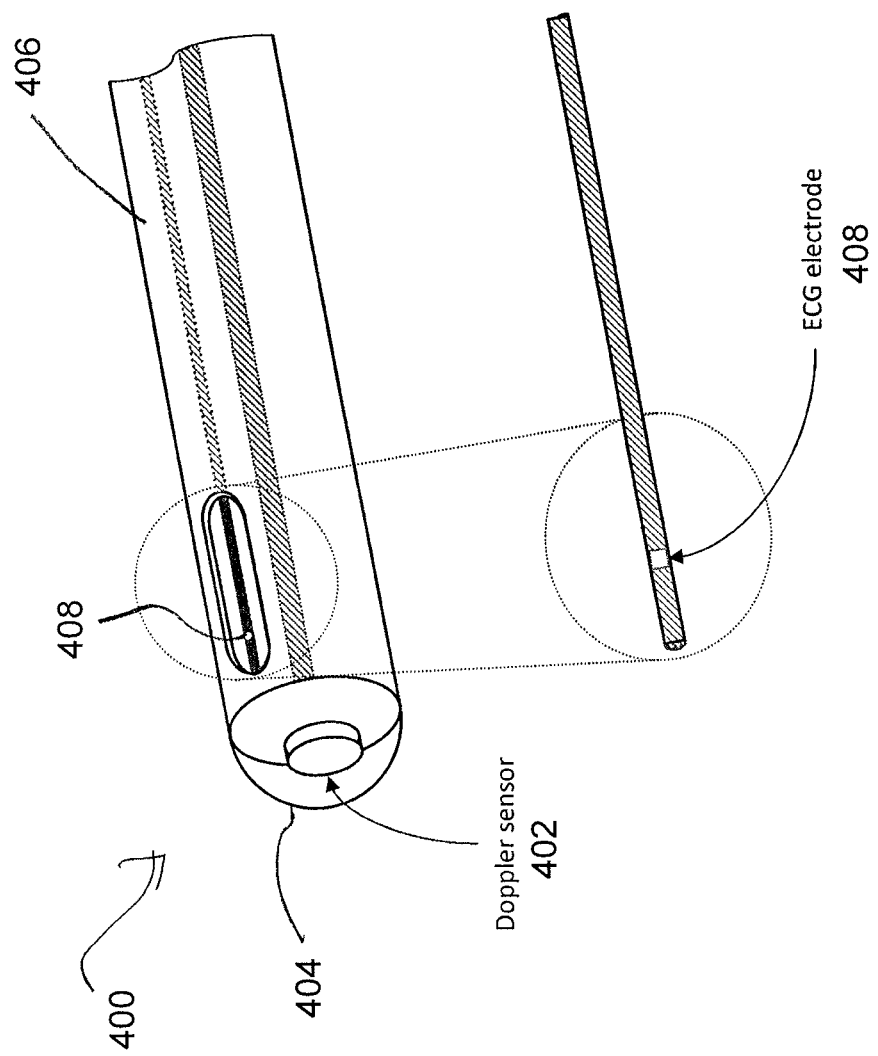
FIG. 4 shows a stylet with an embodiment of an intravascular ECG electrode and an ultrasound Doppler sensor.

To increase accuracy of the catheter tip placement, an endovenous access and guidance system 400 with an ultrasound Doppler transducer 402 on the distal end 404 of a stylet 406 and an intravascular ECG electrode 408 on the side of the stylet 406, as illustrated in FIG. 4, can be used. The use of non-imaging ultrasound Doppler and ECG for the catheter tip placement is described in U.S. application Ser. No. 13/292,010, filed Nov. 8, 2011, entitled "Endovascular Navigation System and Method", which is hereby incorporated by reference in its entirety for all purposes. In some embodiments, a processor computes in vivo non-image based ultrasound information of venous blood flow and ECG of the patient provided by the ultrasound and ECG sensors. This provides catheter tip location information computed by a novel Fuzzy-logic algorithm, for example, and displays the estimated catheter tip location on the output device as symbol.

Fuzzy logic is based on the way how the brain deals with ambiguous input information to make a meaningful conclusion. Fuzzy logic has a several advantages, such as 1) mimicking human decision making rules to handle vague, impression, and imperfect information and 2) modeling of non-linear and complex problems. However, Fuzzy logic has several disadvantages. First, it is highly abstractive. Second, Fuzzy logic has to be carefully and sophisticatedly designed to discover the true relationship between input and output data. Third, Fuzzy logic has a lack of self learning mechanisms.

Due to the limitations of Fuzzy logic and the uncharacteristic nature of physiological data of some patients, a solely Fuzzy logic based tip detection algorithm may result in unexpected or inaccurate results. In this application, we overcome the limitations and disadvantages listed above of conventional and other known systems and methods. We improve methods to optimize the use of ECG and ultrasound Doppler signals and process the distinctive physiological features using a Neuro-Fuzzy system algorithm, where Neuro-Fuzzy refers to a combination of artificial neural networks and fuzzy logic in the field of artificial intelligence.

The present invention provides new data processing algorithms for intravascular guidance and placement of an endovascular catheter based on the analysis of venous blood flow patterns using an ultrasound Doppler technique and the analysis of intravascular and external ECG. The present invention overcomes the above described limitations of the conventional and currently available guidance systems, and provides improved accuracy of the guidance system. The output device of the guidance system provides guiding and positioning information of an endovascular catheter to a user in the form of navigation instructions.

SVC Indicator

The present invention is based on the understanding that each location of the major venous vasculature from the peripheral arm vein or other peripheral vein to the heart can be identified by specific blood flow patterns quantified by ultrasound Doppler and by specific ECG features. The direction of the catheter's navigation can be determined by relativespectral power analysis (antegrade vs. retrograde) of blood flow direction measured by the Doppler sensor, and by monitoring and/or measuring the change of the major ECG components.

For example, in the case of a CVC or PICC line, by real-time monitoring of the direction and speed of blood flow in the venous system, a user can estimate the catheter tip location and guide the CVC or PICC to the ideal or target location (i.e. ⅓ lower SVC 102 to CAJ 104). FIG. 1 illustrates the anatomical location of the CAJ 104, which is located between the SVC 100 and RA 106.

In patients with atrial fibrillation/flutter, the atrial electrical activity (the P wave) is distorted and may not be seen on the regular external skin ECG which limits using of P wave morphology for catheter guidance. The P wave may become visible as the intravascular ECG electrode approaches the CAJ and RA. However, the atrial arrhythmias limit use of P wave information (the amplitude and morphological changes of the atrial electrical activity) that can be extracted even though the intravascular ECG electrode is placed in the CAJ or RA.

Since the ventricular electrical potential change, as shown in the QRS complex, is larger than that of the P wave of the atrium, the changes in the ventricular electrical potential can be detected more distally from the heart (e.g., the beginning or upper portion of the SVC) while the atrial electrical potential change can be detected only more proximally from the heart (e.g., the lower ⅓ SVC). Since the end of the SVC proximal to the heart forms the CAJ, placement of the catheter into the SVC is one key step for ideal or target location placement. Therefore, monitoring the changes in the ventricular electrical potential from the intravascular ECG will provide additional navigational information such as the location of the SVC, such as the upper portion of the SVC, especially in individuals with atrial arrhythmias.

In some embodiments, a processor with memory incorporates a set of rules and/or instructions to detect the SVC area within the vasculature of the patient. In some embodiments, the instructions can be implemented on an application specific integrated circuit (ASIC). In the beginning (or during the calibration session), based on the QRS complex amplitude of an ensemble averaged ECG waveform, a QRS complex amplitude ratio threshold value, using for example the peripheral vein ECG waveform as the reference, can be assigned as follows:

1) If QRS amplitude is greater than or equal to Threshold 1, the QRS complex amplitude ratio threshold is 140(%)
2) If QRS amplitude is greater than or equal to 0.5*Threshold 1 but less than Threshold 1, the QRS complex amplitude ratio threshold is 160(%)
3) If QRS amplitude is less than 0.5*Threshold 1, the QRS complex amplitude ratio threshold is 180(%)

For example, Threshold 1 can be 400 ADC counts or the corresponding voltage. The ensemble averaged ECG waveform is an averaged ECG waveform from multiple external (from skin) ECG waveforms that can be aligned based on the R wave. The ensemble averaged ECG waveform generally has less noise than a raw waveform, but the ensemble averaged ECG waveform is not an artificially filtered signal. The ensemble averaged ECG waveform can be created during the calibration session. Once a noise-reduced ensemble averaged ECG signal is created, the QRS complex amplitude can be measured and saved into the memory for comparison with a QRS complex amplitude of the intravascular ECG, measured from the stylet for example. Beat-to-beat QRS complex amplitude ratio between intravascular and external ECG can be monitored. The QRS complex amplitude ratio can be defined as the amplitude of the intravascular ECG divided by the amplitude of the external ECG, which can be Lead II for example. If the current beat's ratio and 3 or more other previous beats' ratios are higher than the threshold value, it is considered as a SVC area, and the SVC flag is saved in the computer memory. In other embodiments, if 2 or more of the previous beats' ratios are higher than the threshold value, it is considered as a SVC area. Using additional beat ratios can decrease erroneous detection of the SVC and increase the accuracy of the system, but collecting the extra beat ratios may increase the time it takes to make the determination.

Figure 5:
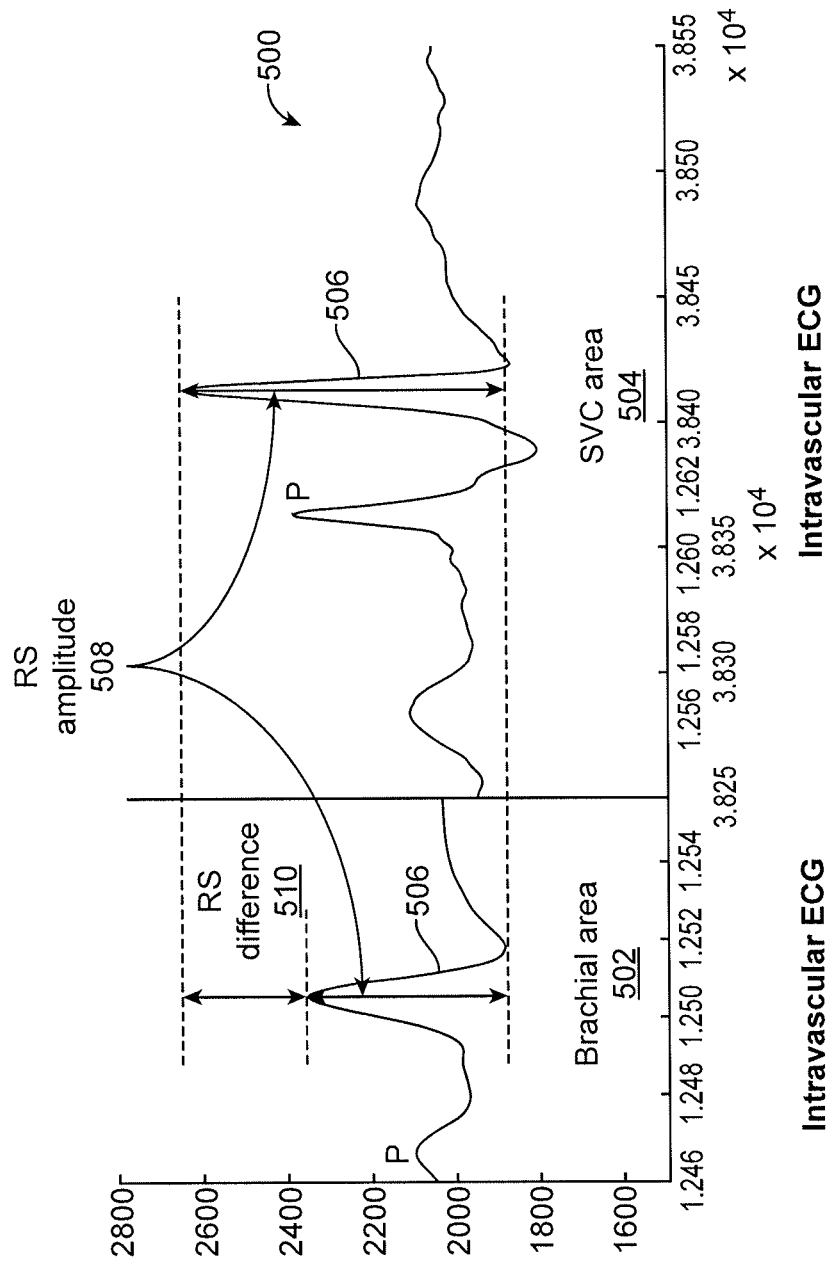
FIG. 5 shows a QRS complex amplitude comparison between the brachial area versus the superior vena cava (SVC) area.
Figure 6:
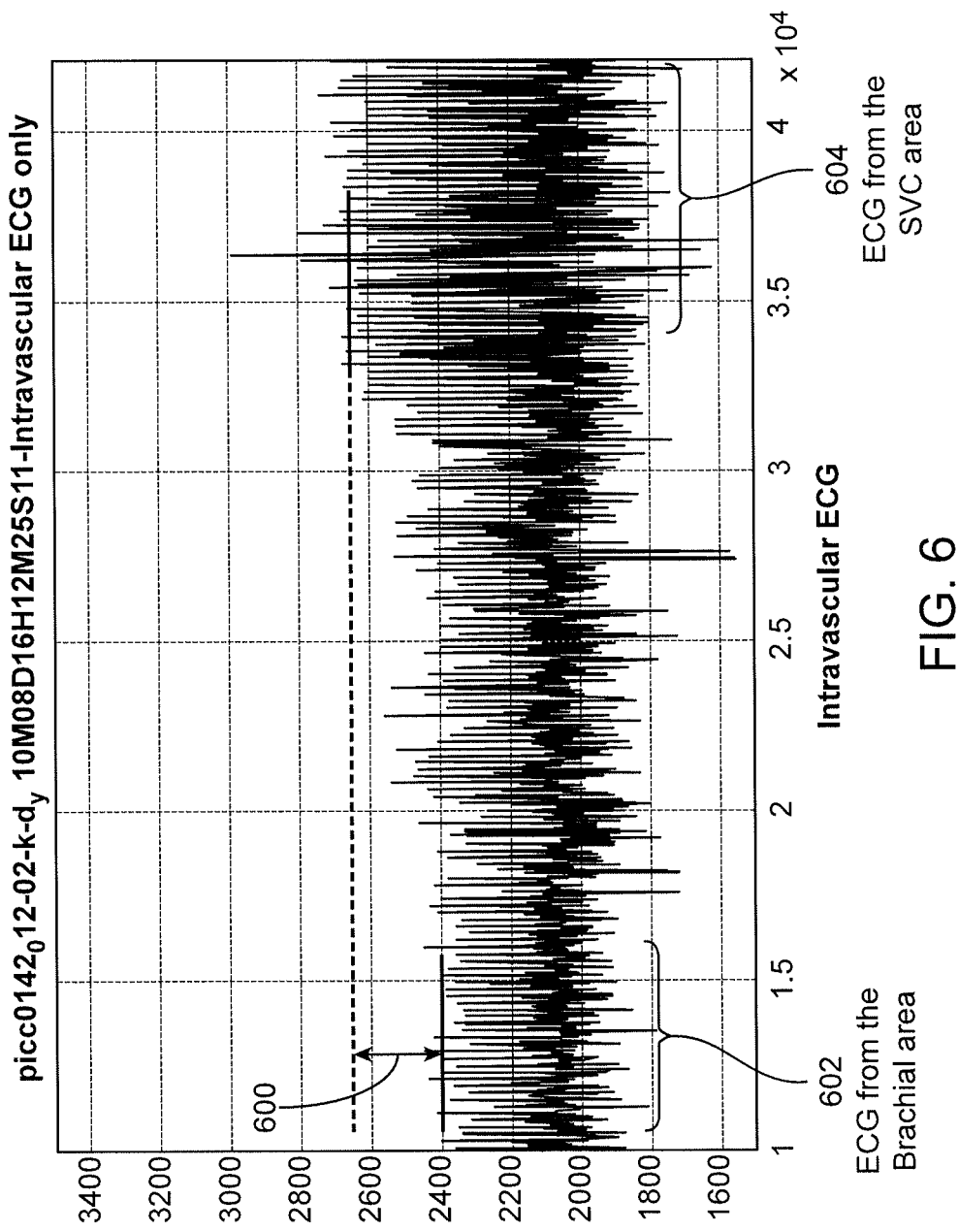
FIG. 6 shows an example of QRS complex change as the sensor moves towards the heart.

FIG. 5 illustrates typical ECG waveform examples 500 measured from the brachial area 502 and the SVC area 504 showing that the amplitude change of the QRS complex 506 is visible. For example, the amplitude change can be defined as the difference 510 in the RS amplitudes 508 between the two waveforms. FIG. 6 illustrates an exemplary data set showing the ECG amplitude change 600 as the intravascular ECG electrode navigates through the venous vasculature pathway from the brachial area 602 to the SVC area 604.

In some embodiments, additional features from the ECG waveform can be extracted and used to identify the SVC area and the CAJ area, which is the junction between the SVC and RA. In some embodiments, these additional features can be used to distinguish between the SVC and CAJ. For example, with reference to FIGS. 11A-11C which illustrate exemplary ECG waveforms from two different patients from the CAJ and FIG. 11C which illustrates an exemplary ECG waveform from the SVC, in addition to the QRS complex amplitude, (1) the amplitude difference or ratio between R and S waves, (2) the amplitude difference or ratio between the R wave and the isoelectric line, (3) the area under the QRS waveform, (4) the T wave amplitude, (5) the amplitude difference or ratio between the T wave and other ECG features including but not limited to the P wave, the QRS complex, the R wave and the S wave, (6) the area under the T waveform, and (7) various relationships of the ECG features listed herein, such as T wave amplitude versus QRS amplitude, area under the various portions of the ECG waveform, slopes of various portions of the ECG waveform, amplitude differences and/or ratios between the different features of the ECG waveform such as P wave to R wave amplitude difference or ratio, and the like, can all be used to refine the location of the stylet within the SVC and CAJ.

Figure 11A:
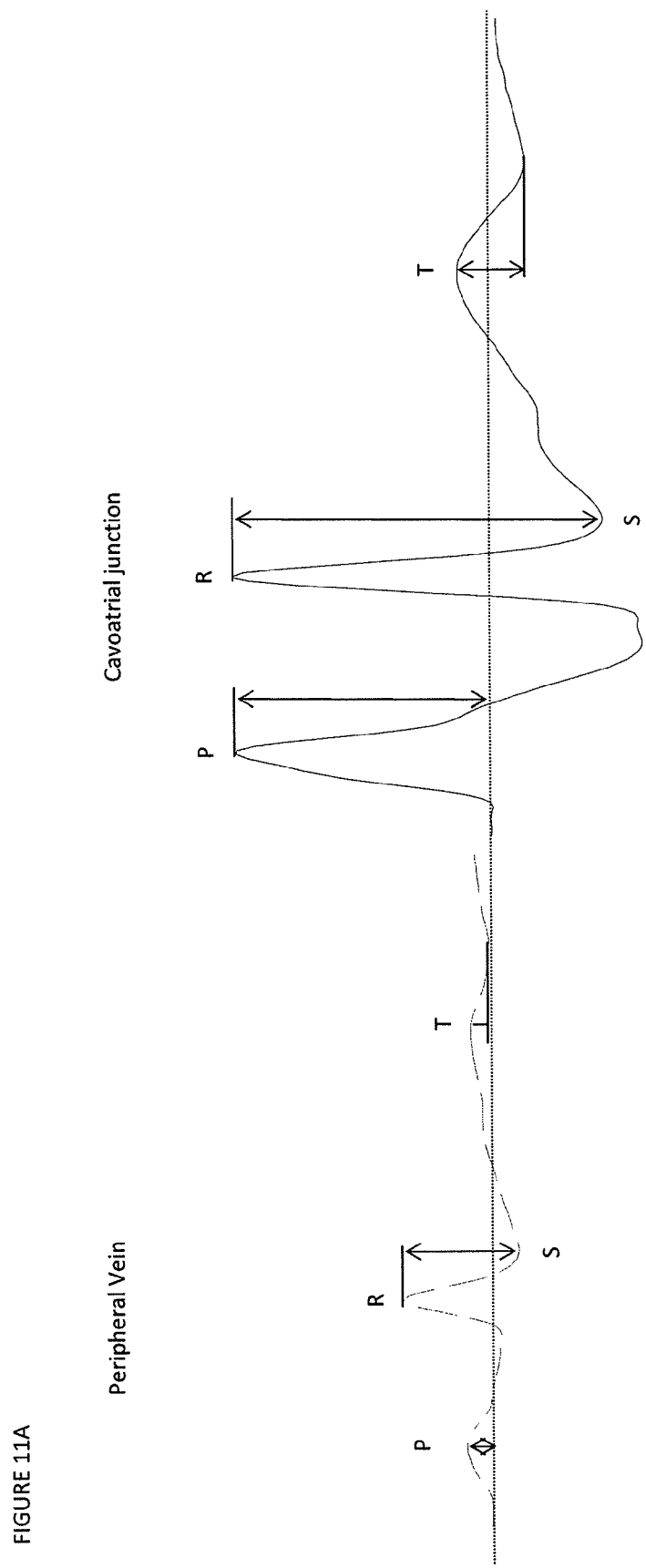
FIGS. 11A and 11B illustrate the ECG waveforms of two exemplary patients in both a peripheral vein and at the CAJ.
Figure 11B:
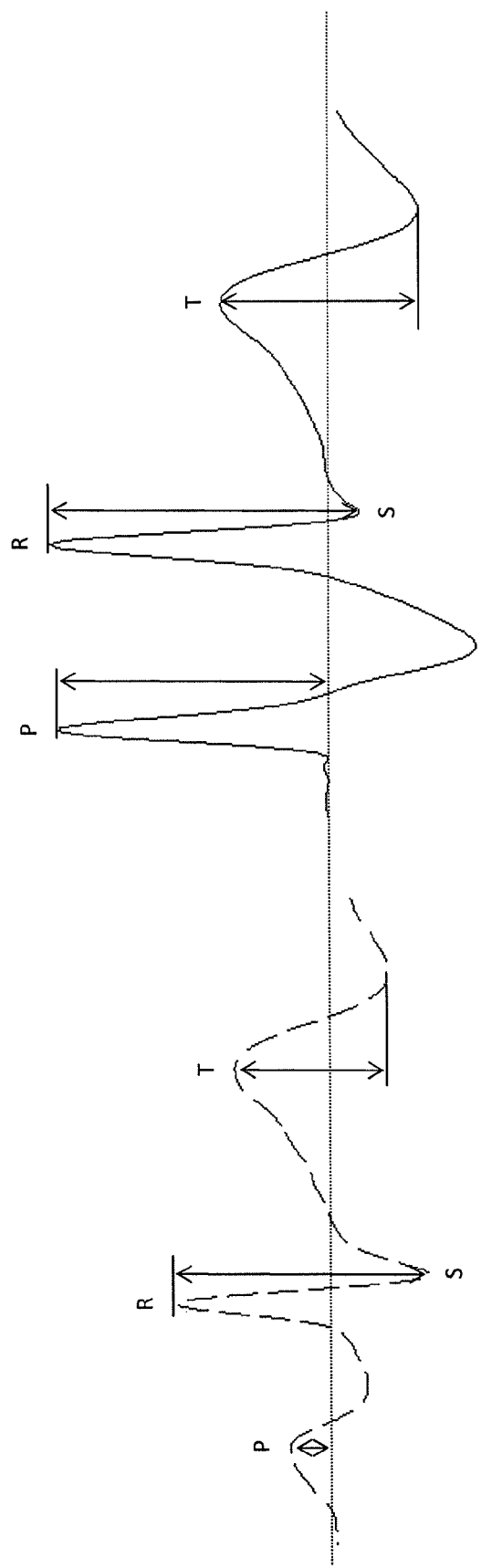
Figure 11C:
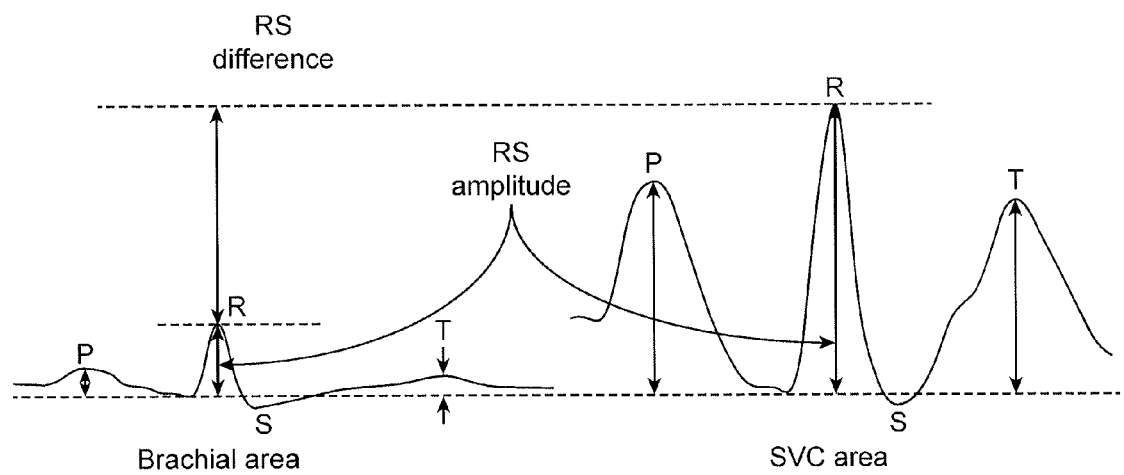
FIG. 11C illustrates an exemplary ECG waveform from the brachial area and the SVC area.

For example, an analysis of FIGS. 11A and 11B illustrates that both the T wave amplitude and the P wave amplitude increases between the ECG waveform measured in the peripheral vein and the ECG waveform measured in the CAJ, while an analysis of FIG. 11C also illustrates that both the T wave amplitude and the P wave amplitude can increase from the peripheral vein to the SVC. Comparing the SVC and CAJ waveforms, the difference between the P wave amplitude and the RS amplitude is less in the CAJ waveform than the SVC waveform, which can allow the system and method to distinguish between the SVC and CAJ. In general, the system and method identifies differences between the ECG waveforms in the peripheral vein and the location of interest, such as the SVC, CAJ or other location, which are consistently found among a large population of patients. These consistently identified relationships can be incorporated in the features, parameters, constants and algorithms described herein to help locate the stylet.

In some embodiments, the ratio of the beat-to-beat feature value to an initial feature value is compared with a threshold feature value, where the beat-to-beat feature value refers to the present or current feature value during the navigation procedure, the initial feature value refers to the feature value measured after insertion of the stylet or during initial calibration, and the threshold value is a value determined from a database of patient data such that when the ratio exceeds the threshold, it is likely that the stylet is in the SVC or some other target location.

In addition, in some embodiments, the values of the initial feature value and/or the value of the threshold feature value can be constrained to a predetermined range. In some embodiments, the threshold feature value can be a predetermined constant. For example, one or more of a lower bound and a higher bound can be set for the initial feature value and/or the threshold feature value. For example, the above relationships can be expressed in equations such as the following, which uses the QRS amplitude as an example:

$$QRS_{init} = \begin{cases} A_1 & QRS_{init} \leq A_1 \\ QRS_{init} & A_1 < QRS_{init} < B_1 \\ B_1 & QRS_{init} \geq B_1 \end{cases}$$

$$QRS_{Thres} = \begin{cases} \alpha_1 & QRS_{init} \leq A_1 \\ \alpha_2 & A_1 < QRS_{init} < B_1 \\ \alpha_3 & QRS_{init} \geq B_1 \end{cases}$$

If $\frac{QRS_{Beat-to-beat}}{QRS_{init}} \geq QRS_{Thres}$, show SVC sign

These equations specify that the initial QRS value has a value between $A_1$ and $B_1$, which can be constants with predetermined values. This means that when the initial QRS value is being determined, during for example the calibration procedure, and the measured QRS value is less than $A_1$, then the initial QRS value is assigned a value of $A_1$. If the measured QRS value is between $A_1$ and $B_1$, the initial QRS value is assigned a value of the measured QRS value, and if the QRS value is greater than $B_1$, then the initial QRS value is set at $B_1$.

Figure 12:
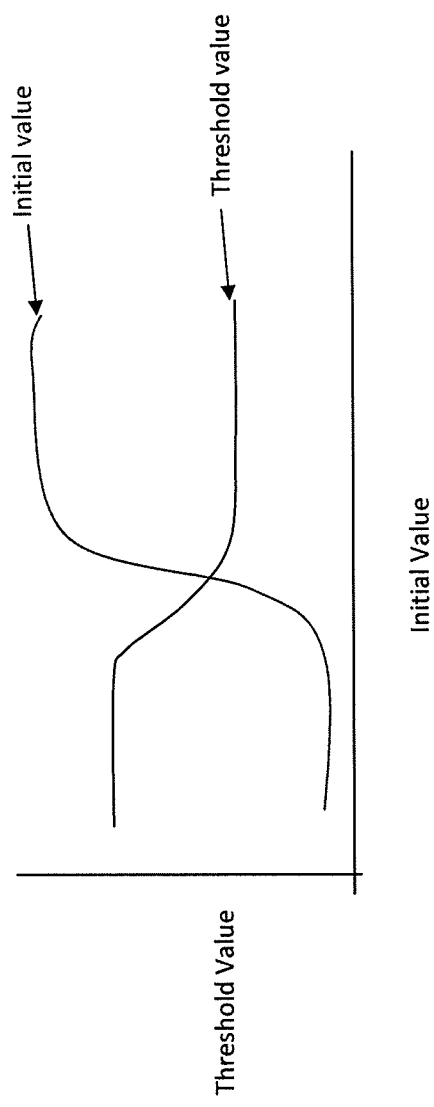
FIG. 12 illustrates an embodiment of the relationship between the initial feature value and the threshold feature value.

In some embodiments, instead of or in addition to using the comparison between the ratio and the threshold, a delta feature value can be determined, where the delta feature value is equal to a product between a sigmoid weighting factor and a value that is a function of the beat-to-beat feature value and optionally other variables, parameters or constants, such as the upper threshold for example, which can also depend on a variety of factors, such as the initial feature value, the signal strength or quality, and the like. The delta feature value can be compared with the threshold feature value, where the threshold feature value is selected such that when the delta feature value exceeds the threshold feature value, it is likely that the stylet is in the SVC or some other target location. The value of the sigmoid weighting factor can depend on, i.e. can be a function of, the initial feature value and/or other variables. Similarly, the threshold feature value can depend on, i.e. can be a function of, the initial feature value and/or other variables, as illustrated in FIG. 12. The following equations represent these relationships:

$$F_\Delta = Weight_{sigmoid} \times f(X, F_{Beat-to-beat})$$

If $F_\Delta \geq F_{Thres}$, high probability to show SVC or blue bulls eye sign An aspect of the invention includes 1) a pre-processor manipulation of the ECG and non-imaging ultrasound Doppler signal to remove signal noise and extraction of information related to key physiological features, and 2) a processor which can a) evaluate ECG features to generate SVC location information and b) process extracted ECG and Doppler features using the Neuro-Fuzzy system to guide an endovascular catheter to the desired location.

The computer-readable set of rules for ECG waveform (both intravascular and external ECG) includes:
1. Rules to evaluate external ECG waveforms and generate an ensemble averaged ECG waveform
2. Rules to evaluate and measure external ECG P wave amplitude, QRS complex amplitude, T wave amplitude, and intervals (i.e., PR, RR, and QT interval) on the ensemble averaged ECG waveform, and other features as described herein
3. Rules to evaluate the underlying rhythm of the ECG.

In some embodiments, as few as five ECG waveforms are needed to fully satisfy the above rules and to generate an accurate ensemble averaged ECG waveform. In other embodiments, less than five ECG waveforms can be used to satisfy the above rules. In other embodiments, more than five ECG waveforms can be used to satisfy the above rules. In some embodiments, the ECG waveforms used for ensemble averaging are consecutive waveforms, i.e. from consecutive heart beats.

The computer-readable set of rules is also designed to evaluate external and intravascular ECG waveforms and classify ECG waveforms into the following categories: 1) noise data, 2) normal ECG data, 3) noisy ECG data, 4) abnormal ECG data due to abnormal heart conditions, and 5) atrial fibrillation/flutter. Depending on the classification result, an appropriate peak detection algorithm is assigned to derive accurate results. In addition, the classification of the data can affect the values of the thresholds, the weighting factors, the values of the lower and upper bounds, and other constants and parameters.

In general, correlation of beat-to-beat ECG waveforms (ensemble averaged ECG vs. external ECG, ensemble averaged ECG vs. intravascular ECG, external ECG vs intravascular ECG, previous vs. current beat of external ECG, previous vs. current beat of intravascular ECG) are tested and compared. In some embodiments, the comparison results (e.g., correlation coefficient) are used as input parameters to an ECG waveform classification algorithm, which can be Neuro-Fuzzy logic based, and only meaningful waveforms from the waveform classification algorithm are processed to increase the accuracy of the current algorithm. If the external ECG waveform has a higher score than the intravascular ECG waveform at the same beat, the external ECG is processed to detect ECG peaks and interval information. In some embodiments, the ECG waveform with the higher score is used for further processing. Afterwards the ECG peak detection algorithm detects intravascular ECG peak information based on the detected external ECG peak locations. If intravascular ECG waveform has a higher score than intravascular ECG waveform, only peaks and interval information of intravascular ECG are computed.

SVC area detection procedures include:
1) The QRS amplitude and other features as described herein of the external ECG is measured and a threshold value is assigned
2) Beat-to-beat QRS amplitude ratio between intravascular ECG and external ECG is calculated as well as the beat-to-beat ratios of the other features
3) Beat-to-beat SVC area is estimated with the follow criteria:
   If QRS amplitude of external ECG is greater than or equal to Threshold 1, the QRS amplitude ratio ((intravascular ECG/external ECG)*100) has to be greater than or equal to 140(%).

If QRS amplitude of external ECG is greater than or equal to 0.5*Threshold 1 but less than Threshold 1, the QRS amplitude ratio has to be greater than or equal to 160(%).

If QRS amplitude of external ECG is less than 0.5 Threshold 1, the QRS amplitude ratio has to be greater than or equal to 180(%).

4) SVC area detection result by chance is eliminated or reduced by analyzing the last 5 beats' information. In other embodiments, 4, 3, or 2 of the last beats can be analyzed to reduce error. In other embodiments, more than 5 of the last beats can be analyzed to reduce error.

Overall System and Method

Figure 7:
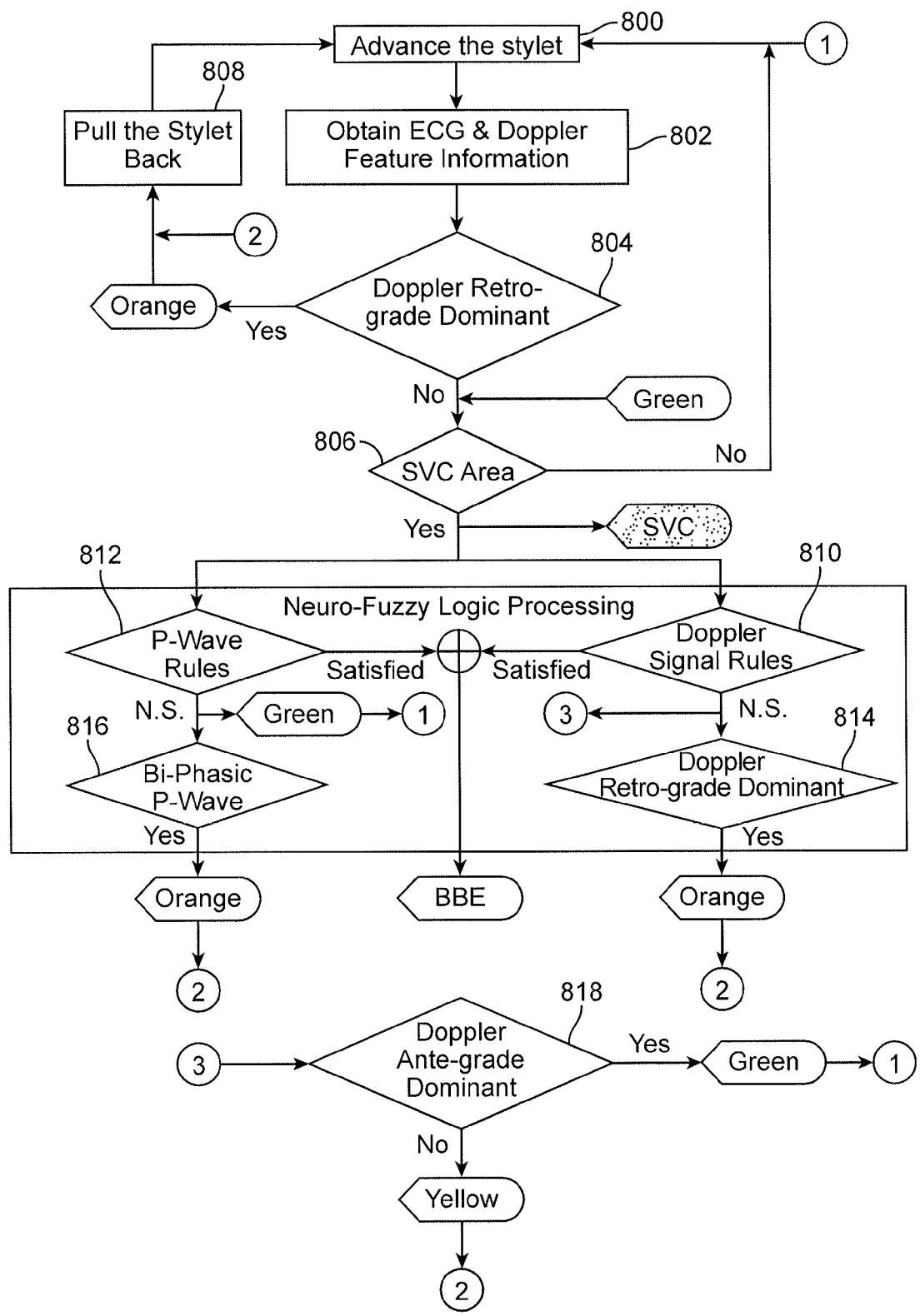
FIG. 7 shows a flow chart describing generally an embodiment of the navigation process.
Figure 8:
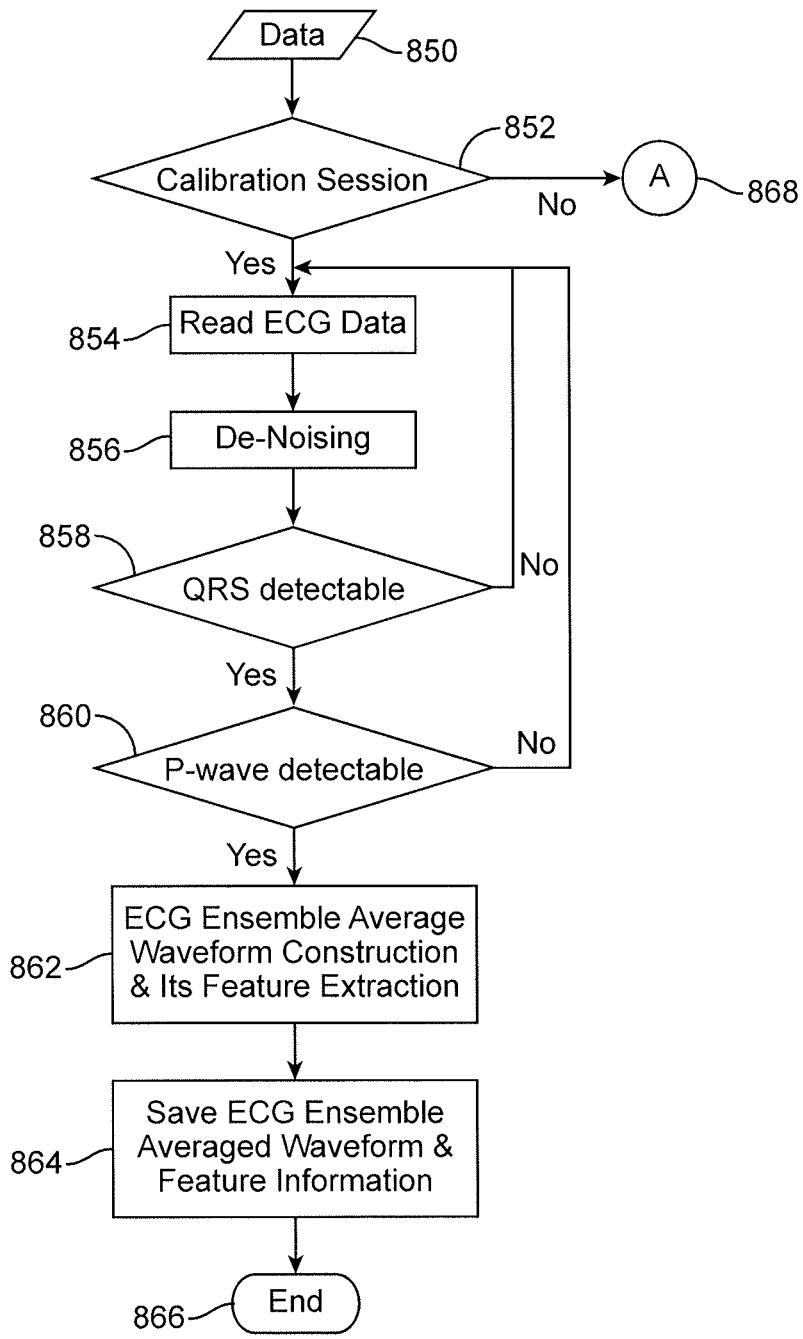
FIG. 8 shows a flow chart of an embodiment of the calibration process.

With the system algorithm, which can be based on Neuro-Fuzzy logic, extracted features are processed and a weighing factor is assigned to each feature based on the evaluation of ECG, acoustic and Doppler signals. In some embodiments, a subset of the above features, such as one, two or more features, can be used for the analysis. For example, in one embodiment of the algorithm, the preprocessor conducts high-level feature extraction processing of the data. The processor implements the algorithms to make the final decision of the catheter location. During the catheter insertion with the stylet, the guidance system provides four different location indicators: a green arrow (move forward), the blue bull's eye (right location), a red or orange indicator (stop and pull back), and yellow triangle (no decision due to the lack of data). These location indicators guide the clinical operator to place the catheter in the optimal location. FIGS. 7 and 8 illustrate simplified general steps for catheter guidance according to various embodiments.

Additionally, the location of the catheter tip may provide a gating function for the processor such as changing the weights, parameters, features and formulas of the algorithms based on the current location of the catheter tip to increase the accuracy of the placing the catheter tip in the ideal or desired location. For example, if the processor can determine the location of the SVC, then the processor knows any turbulent signals found will be associated with the RA since the stylet tip has already passed all ancillary venous junctures. Therefore, the weighting and/or features of the state functions can be changed to reflect this information.

As illustrated in FIG. 7, the method begins after the insertion of a stylet, catheter or other device into a peripheral vein of the patient with step 800, where the stylet is advanced. Then, at step 802, ECG and Doppler feature information is obtained. Using this information, at step 804 the system determines using the Doppler data whether retrograde flow is dominant. If retrograde flow is dominant, the system activates the red/orange indicator which prompts the user to go to step 808 and pull the stylet back and then start over at step 800. If, however, flow is not retrograde dominant, the system activates the green indicator, the stylet is advanced, and the system checks whether the SVC area has been reached at step 806. If the SVC has not been reached, the green indicator is activated and the stylet is advanced. If however the system determines that the SVC area has been reached, the system proceeds to evaluate Doppler signal rules at step 810 and P wave rules at step 812. If both sets of rules are satisfied, then the target location (i.e., ⅓ lower SVC) has been reached and the blue bull's eye indicator can be activated.

If however, the Doppler signal rules have not been satisfied, the system determines whether the flow is retrograde dominant or antegrade dominant using the Doppler data. If the flow is retrograde dominant 814, the red/orange indicator is activated, which instructs the user to pull the stylet back, which sends the process back to step 800. If the flow is clearly antegrade dominant, then the green indicator is activated, which instructs the user to advance the stylet, sending the process back to step 800. If the flow is not clearly antegrade dominant, the yellow indicator is activated, which instructs the user the wait and sends the process to step 808.

If however, the P wave rules are not satisfied, the system determines whether the P wave is biphasic 816. If the P wave is biphasic, the red/orange indicator is activated, which instructs the user to stop and pull back, and the process is directed to step 808. If the P wave is not biphasic, then the green indicator is activated, which instructs the user to advance the stylet and returns the process to step 800.

FIG. 8 illustrates a calibration procedure. Starting at step 850, ECG data is obtained. Then at step 852 the system determines whether the ECG data was collected as part of a calibration or not. If not, the ECG data is sent for pre-processing and processing 868 as illustrated in FIG. 10. If a calibration session is indicated, the process proceeds to step 854 where the ECG data is read, then de-noised at step 856, and sent to step 858 to determine whether the QRS complex is detectable. If not, the process is sent back to step 854 and the next ECG data is read. If the QRS complex is detectable, the process proceeds to step 860 where the system attempts to detect the P wave. If the P wave is not detectable, the process is sent back to step 854. If the P wave is detectable, the process proceeds to step 862 where the system constructs an ECG ensemble average waveform and extracts the ECG features. Then the process proceeds to step 864, where the ECG ensemble average waveform and extracted features are saved, which ends the calibration session 866.

Figure 9:
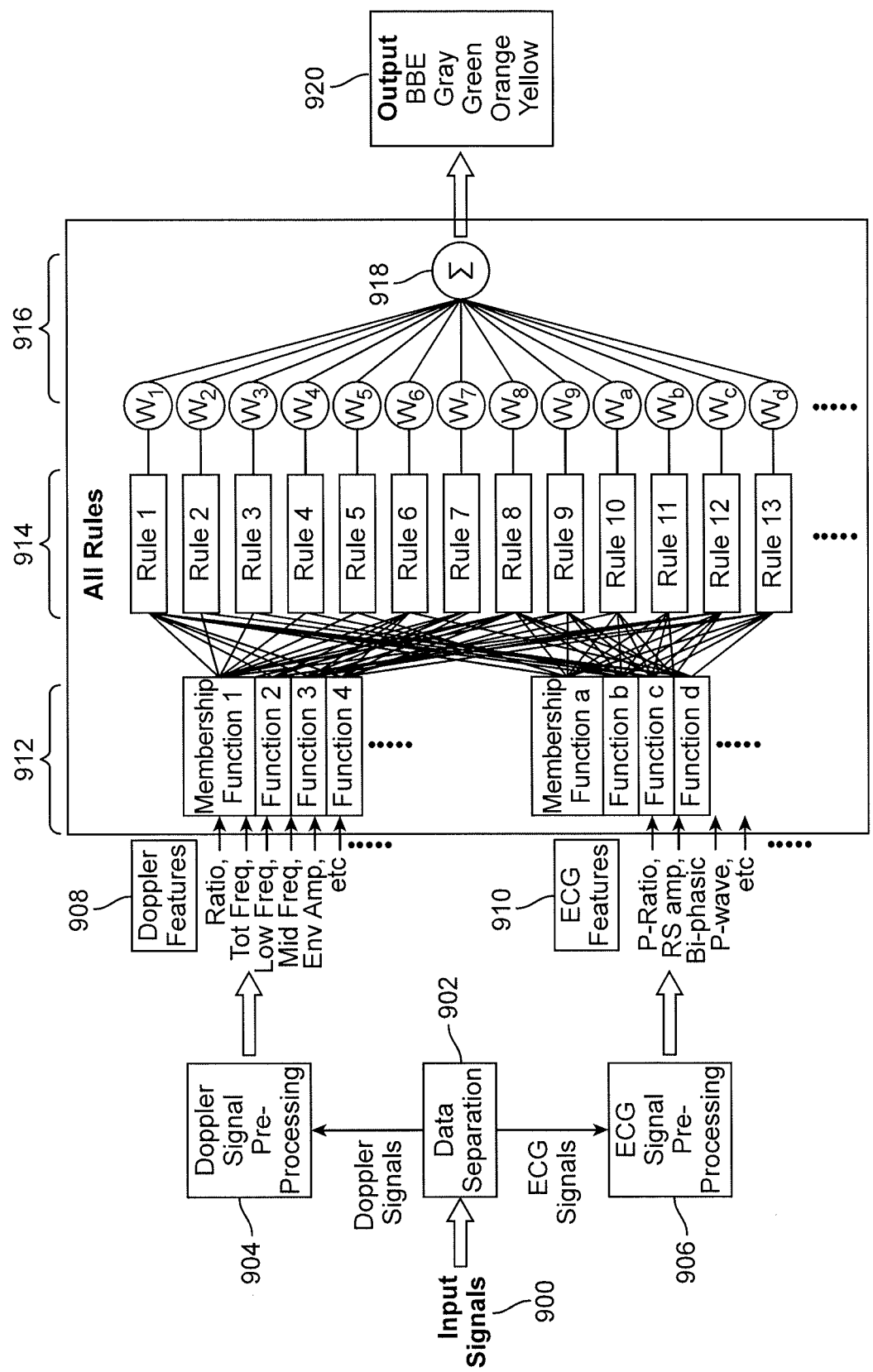
FIG. 9 shows an embodiment of the processing of data.

FIG. 9 illustrates a diagram of the logic process, which can be Neuro-Fuzzy, of the collected ECG and Doppler data, which are further described herein and in U.S. application Ser. No. 13/292,010. As shown in FIG. 9, in some embodiments, input signals 900 undergo data separation 902 into Doppler signals, which undergo Doppler signal pre-processing 904, and ECG signals, which undergo ECG signal pre-processing 906. From the Doppler signals, Doppler features are extracted 908 and from the ECG signals, ECG features are extracted 910. The extracted features are sent to membership functions 912 which are incorporated into a plurality of rules 914. Each rule is given a weighting factor 916 which can be state dependent (i.e., state 1 (green), state 2 (red/orange), state 3 (yellow), state 4 (blue), etc). Each state can be a function of the membership functions, rules and weights 918. The state function with the highest score can be output to the user 920.

In various embodiments, both ECG and Doppler based processing for guiding and positioning of the stylet include the following operations which are illustrated in FIG. 10:

If it is the calibration session (FIG. 8B):
1. Get intravascular and external ECG signal, remove noise signal and
2. Detect P-wave and QRS complex,
3. Generate ECG ensemble average waveform;

If it is the PICC navigation session (FIG. 10):
1. Get intravascular and external ECG signal,
2. Remove noise signal from the ECG signals,
3. Detect QRS complex,
4. Calculate magnitude of QRS complex,
5. Detect P-wave,
6. Calculate magnitude and time location of the P-wave,
7. Calculate the ratio of intravascular QRS complex magnitude to external QRS complex magnitude,
8. Calculate the ratio of intravascular P-wave magnitude to external P-wave magnitude,
9. Detect the biphasic P-wave and send out a flag (internal software flag), 10. Get antegrade and retrograde blood flow Doppler data,
11. Apply filters on the Doppler data,
12. Calculate frequency spectrum of Doppler data,
13. Display time-frequency spectrum data,
14. Construct the envelop curve of the spectrum data,
15. Extract Doppler features,
16. Calculate the membership functions for the Doppler signal features and ECG signal features,
17. Assign weight to each features,
18. Calculate the final score for each possible sign,
Display sign with the highest score in each cardiac cycle.

Variations and modifications of the devices and methods disclosed herein will be readily apparent to persons skilled in the art. As such, it should be understood that the foregoing detailed description and the accompanying illustrations, are made for purposes of clarity and understanding, and are not intended to limit the scope of the invention, which is defined by the claims appended hereto. Any feature described in any one embodiment described herein can be combined with any other feature of any of the other embodiments whether preferred or not.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method for determining the location of a portion of a medical device within a body, the method comprising:
    inserting at least part of the medical device into the venous vasculature of the body;
    measuring an initial electrocardiogram waveform using an intravascular electrocardiogram electrode following the insertion;
    advancing the medical device within the venous vasculature of the body;
    measuring a second electrocardiogram waveform using the intravascular electrocardiogram electrode following the advancement of the medical device;
    extracting an initial amplitude of the R wave and an initial amplitude of the S wave from the initial electrocardiogram waveform;
    extracting a beat-to-beat amplitude of the R wave and a beat-to-beat amplitude of the S wave from the second electrocardiogram waveform;
    determining a first difference between the initial amplitude of the R wave and the initial amplitude of the S wave;
    determining a second difference between the beat-to-beat amplitude of the R wave and the beat-to-beat amplitude of the S wave;
    determining a ratio of the first difference between the initial amplitude of the R wave and the initial amplitude of the S wave and the second difference between the beat-to-beat amplitude of the R wave and the beat-to-beat amplitude of the S wave;
    comparing the ratio with one or more predetermined threshold feature values; and
    determining whether the portion of the medical device is at the superior vena cava of the body based on the comparison of the ratio with the one or more threshold feature values.

2. The method of claim 1, further comprising:
    measuring an external electrocardiogram waveform using an external electrocardiogram electrode;
    extracting an external amplitude of the R wave and an external amplitude of the S wave from the external electrocardiogram waveform; and
    determining a third difference between the external amplitude of the R wave and the external amplitude of the S wave of the external electrocardiogram waveform.

3. The method of claim 2, further comprising determining a second ratio of the second difference between the beat-to-beat amplitude of the R wave and the beat-to-beat amplitude of the S wave to the third difference between the external amplitude of the R wave and the external amplitude of the S wave.

4. The method of claim 3, wherein determining that the portion of the medical device is in the superior vena cava is further based on a comparison of the second ratio to an amplitude ratio threshold.

5. The method of claim 4, wherein the amplitude ratio threshold is 1.4.

6. The method of claim 3, wherein determining that the portion of the medical device is in the superior vena cava comprises determining that the ratio is greater than or equal to half of a first threshold but less than the first threshold, and the second ratio is greater than or equal to an amplitude ratio threshold.

7. The method of claim 6, wherein the first threshold is 1.6.

8. The method of claim 3, wherein determining that the portion of the medical device is in the superior vena cava comprises determining that the ratio is less than half of a first threshold, and the second ratio is greater than or equal to an amplitude ratio threshold.

9. The method of claim 8, wherein the first threshold is 1.8.

10. The method of claim 1, wherein the beat-to-beat amplitude of the R wave and the beat-to-beat amplitude of the S wave are extracted from multiple averaged electrocardiogram waveforms.

11. The method of claim 1, wherein the portion of the medical device is a distal portion of the medical device.

12. The method of claim 1, wherein:
    measuring the second electrocardiogram waveform using the intravascular electrocardiogram electrode comprises measuring five or more second electrocardiogram waveforms using the intravascular electrocardiogram electrode; and
    extracting the beat-to-beat amplitude of the R wave and the beat-to-beat amplitude of the S wave from the second electrocardiogram waveform comprises extracting the beat-to-beat amplitude of the R wave and the beat-to-beat amplitude of the S wave from an average of the five or more second electrocardiogram waveforms.

13. A system for determining the location of a portion of a medical device within a body, the system comprising:
    an elongate body having an intravascular electrocardiogram electrode disposed on a distal portion of the elongate body, the elongate body being configured to be inserted into the venous vasculature of the body;
    one or more processors configured to receive and process an electrocardiogram signal from the intravascular electrocardiogram electrode; and
    memory for storing instructions, which when executed by the one or more processors, causes the one or more processors to:
        measure an initial electrocardiogram waveform using an intravascular electrocardiogram electrode following the insertion;
        measure a second electrocardiogram waveform using the intravascular electrocardiogram electrode following advancement of the medical device;

extract an initial amplitude of the R wave and an initial amplitude of the S wave from the initial electrocardiogram waveform;

extract a beat-to-beat amplitude of the R wave and a beat-to-beat amplitude of the S wave from the second electrocardiogram waveform;

determine a first difference between the initial amplitude of the R wave and the initial amplitude of the S wave;

determine a second difference between the beat-to-beat amplitude of the R wave and the beat-to-beat amplitude of the S wave;

determine a ratio of the first difference between the initial amplitude of the R wave and the initial amplitude of the S wave and the second difference between the beat-to-beat amplitude of the R wave and the beat-to-beat amplitude of the S wave;

compare the ratio with one or more predetermined threshold feature values; and determine whether the portion of the medical device is at the superior vena cava of the body based on the comparison of the ratio with the one or more threshold feature values.

14. The system of claim 13, wherein the portion of the medical device is the distal portion of the medical device.

15. The system of claim 13, wherein the one or more processors are configured to:

measure the second electrocardiogram waveform using the intravascular electrocardiogram electrode by measuring five or more second electrocardiogram waveforms using the intravascular electrocardiogram electrode; and extract the beat-to-beat amplitude of the R wave and the beat-to-beat amplitude of the S wave from the second electrocardiogram waveform by extracting the beat-to-beat amplitude of the R wave and the beat-to-beat amplitude of the S wave from an average of the five or more second electrocardiogram waveforms.

* * * * *